(12) United States Patent
Tournefier et al.

(10) Patent No.: US 8,965,497 B2
(45) Date of Patent: Feb. 24, 2015

(54) ELECTROPHYSIOLOGICAL ANALYSIS SYSTEM AND METHOD

(75) Inventors: Annick Nicole Lydie Tournefier, Fontaine Francaise (FR); Philippe Brunswick, Paris (FR); Nicolas Bocquet, Chatillon (FR)

(73) Assignee: Impeto Medical, Paris (FR)

( * ) Notice: Subject to any disclaimer, the term of this patent is extended or adjusted under 35 U.S.C. 154(b) by 1296 days.

(21) Appl. No.: 11/922,812

(22) PCT Filed: Jun. 22, 2006

(86) PCT No.: PCT/EP2006/063452
§ 371 (c)(1),
(2), (4) Date: Jul. 22, 2009

(87) PCT Pub. No.: WO2006/136598
PCT Pub. Date: Dec. 28, 2006

(65) Prior Publication Data
US 2009/0326407 A1    Dec. 31, 2009

(30) Foreign Application Priority Data

Jun. 22, 2005  (FR) ..................... 05 06321
Nov. 29, 2005  (FR) ..................... 05 12068
Feb. 13, 2006  (FR) ..................... 06 01239

(51) Int. Cl.
*A61B 5/053*  (2006.01)
*A61B 5/00*   (2006.01)
*A61B 5/05*   (2006.01)

(52) U.S. Cl.
CPC ............... *A61B 5/0002* (2013.01); *A61B 5/05* (2013.01); *A61B 5/053* (2013.01)
USPC ........................ 600/547; 600/382; 600/393

(58) Field of Classification Search
USPC .......... 600/300, 547, 548; 324/600, 612, 613, 324/691, 692
See application file for complete search history.

(56) References Cited

U.S. PATENT DOCUMENTS 4,690,152 A    9/1987  Juncosa
4,794,934 A *  1/1989  Motoyama et al. ........... 600/547
(Continued)

FOREIGN PATENT DOCUMENTS

WO    WO-00/19894 A1    4/2000
WO    WO-2006136598 A2  12/2006

OTHER PUBLICATIONS

Atkins, Peter, et al.; "Atkins' Physical Chemistry," Eighth Edition, 2006, pp. 1-1053.

(Continued)

*Primary Examiner* — Max Hindenburg
*Assistant Examiner* — John Pani
(74) *Attorney, Agent, or Firm* — Harness, Dickey & Pierce, P.L.C.

(57) ABSTRACT

The invention relates to an electrophysiological analysis system which comprises a plurality of electrodes (E1-E4), power supply means (10, 30) for successively applying a substantially continuous voltage ranging approximately from 1 to 5 volts and lasting from 0.1 to 5 seconds to different slotted electrode pairs, collecting and storing means (450) for recording the variation of a current flow in the electrode pairs to which said voltage slots are applied, means (50) for enabling the current variations obtained by comparison between at least two current variations caused by supposed identical conditions and means (50) for comparing data related to the current variations recorded for several electrode pairs and enabled with reference data. Said invention can be used for chronoamperometrically detecting pathologies, pathological areas and organ dysfunctions.

20 Claims, 3 Drawing Sheets

(56) References Cited

U.S. PATENT DOCUMENTS

Figure 1:
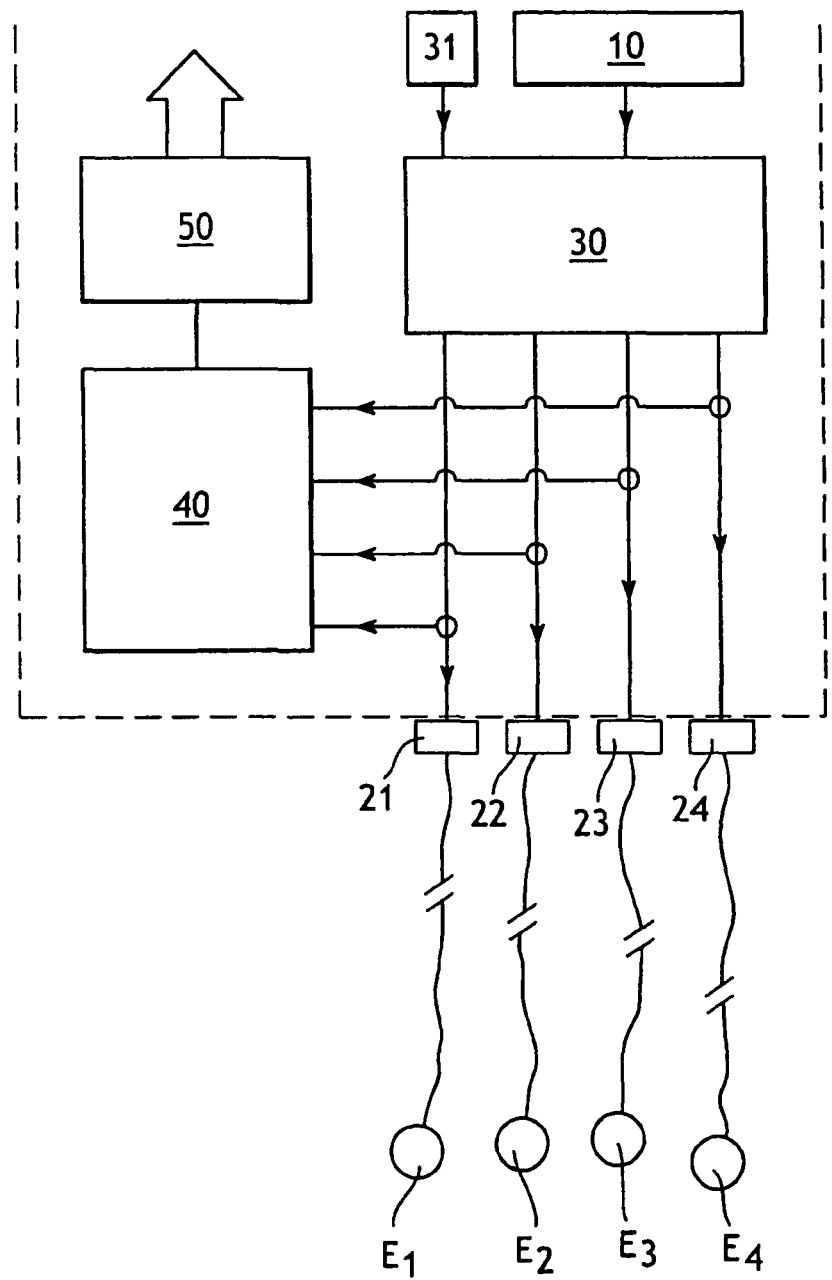

| | | | |
|---|---|---|---|
| 5,406,956 A | 4/1995 | Farwell | |
| 5,427,113 A * | 6/1995 | Hiroshi et al. | 600/547 |
| 5,522,386 A * | 6/1996 | Lerner | 600/547 |
| 5,771,261 A | 6/1998 | Anbar | |
| 5,782,884 A | 7/1998 | Stotts et al. | |
| 5,800,350 A | 9/1998 | Coppleson et al. | |
| 5,947,910 A * | 9/1999 | Zimmet | 600/547 |
| 6,058,325 A * | 5/2000 | Baura | 607/8 |
| 6,491,647 B1 | 12/2002 | Bridger et al. | |
| 6,512,949 B1 | 1/2003 | Combs et al. | |
| 6,517,482 B1 * | 2/2003 | Elden et al. | 600/309 |
| 6,571,124 B1 * | 5/2003 | Storm | 600/547 |
| 6,577,893 B1 | 6/2003 | Besson et al. | |
| 6,871,084 B1 | 3/2005 | Kingsley et al. | |
| 7,931,592 B2 | 4/2011 | Currie et al. | |
| 8,085,144 B2 | 12/2011 | Appelt et al. | |
| 2002/0107452 A1 * | 8/2002 | Kwong | 600/509 |
| 2003/0078505 A1 * | 4/2003 | Kim et al. | 600/485 |
| 2003/0135094 A1 * | 7/2003 | Illyes et al. | 600/300 |
| 2004/0128088 A1 | 7/2004 | Laletin et al. | |
| 2005/0113650 A1 | 5/2005 | Pacione et al. | |
| 2006/0085049 A1 | 4/2006 | Cory et al. | |
| 2006/0122654 A1 * | 6/2006 | Bradley et al. | 607/28 |
| 2006/0127964 A1 | 6/2006 | Ford et al. | |
| 2009/0326407 A1 | 12/2009 | Tournefier et al. | |

OTHER PUBLICATIONS

Cronin, Jane; "Mathematics of Cell Electrophysiology," vol. 63, 1981, p. 23.

Chizmadzhev, Yuri A., et al.; "Electrical Properties of Skin at Moderate Voltages: Contribution of Appendageal Macropores," Biophysical Journal, vol. 74, Feb. 1998, pp. 843-856.

* cited by examiner

ELECTROPHYSIOLOGICAL ANALYSIS SYSTEM AND METHOD

In general, this present invention concerns medical diagnosis appliances in the field of human or animal health.

Given the cost of blood analyses and the invasive character of the taking of blood samples beforehand, physicians are now increasingly reluctant to prescribe excessively frequent full health checks for their patients.

The result is an obvious under-detection of certain illnesses whose detection is mainly achieved by blood analysis, such as diabetes, hypertension, hyperthyroid conditions, and the coronary illnesses.

Moreover when these illnesses are detected, it is often very difficult or costly to assess the effectiveness of the prescribed treatment, since it is impossible in practice to carry out daily biological analyses.

One is also aware of different electrophysiological measurement systems such as electrocardiograph and electroencephalograph appliances. These systems are passive in the sense that they measure the electrical phenomena generated naturally by the human body, which have the advantage of being non-invasive, but whose possibilities in terms of diagnosis are limited.

One is also familiar with so-called active electrophysiological measurement systems based on impedance measurement. The working principle of these appliances is to cause currents to flow between different electrodes placed on the body, and to examine the manner in which certain regions of the body attenuate this current. In fact these techniques, involving quite high frequencies, have the drawback of being strongly dependent on the skin-electrode interface, and in particular on its capacitive effect. The reproducibility of the measurements between patients, or even on a given patient, requires caution in the execution of these high-frequency measurements. For their part, measurements at very low frequencies can well be harmful to the cells.

This present invention aims to broaden the diagnosis possibilities of systems of the electrophysiological type, by enabling them to detect a certain number of illnesses, pathologies, pathological conditions or other problems which are usually detectable by examination of the blood or other bodily fluids.

On this subject, it will be seen that diagnosis systems are already known in which one applies, to electrodes placed on the fingers of one hand, rectangular voltage pulses of a certain frequency, which is necessarily high in order to be able to detect capacitive phenomena on the skin, and then one examines the current flowing in this part of the body in response to this rectangular waveform. This system has evolved to include, in conjunction with the high frequency of the pulses, a Fourier analysis that gives the spectral distribution of the current read.

However this known system has limited application to very localised detection (around the fingers and the toes), and allows diagnosis to be practised only within the limits of conventional acupuncture techniques.

The invention therefore aims to propose a non-invasive diagnosis system that is simple to use, that has a specificity and a sensitivity that are equivalent to laboratory analyses, and that allows the detection, with improved reliability and with a broader range of possibilities regarding certain pathologies, of certain pathological predispositions or certain organ malfunctions.

To this end, the invention proposes an electrophysiological analysis system for the detection of pathologies, characterised in that it includes:

a plurality of surface electrodes designed to be positioned at distant parts of the human body, power means used to apply, in succession, to pairs of different electrodes, essentially continuous voltage pulses of between about 1 and 5 volts and with a length of between about 0.1 and 5 seconds, acquisition and storage means to record the current changes flowing in the electrode pairs as these voltage pulses are applied, means for validation of changes in the acquired current readings by comparison between at least two current changes provoked in conditions that are assumed to be identical, and processing means to compare data relating to the current changes recorded for several electrode pairs and validated against the reference data, and thereby to give an indication of a pathological nature.

Certain aspects, which are preferred but not limiting, of this system are as follows:

the acquisition means are designed to sample the current signal at a rate of about 20 to 10,000 times per second.

the power means are designed to apply, to a given electrode pair, voltage pulses of opposite sign.

the continuous voltage levels of the pulses are adjustable.

the duration of the pulses is adjustable.

the processing means are designed to compare the current changes obtained for several series of voltage pulses applied several times to the electrodes, and to validate these changes if a difference below a given threshold is observed.

the system also includes means to generate graphical representations of the current changes for the different electrode pairs, and corresponding graphical representations of the reference data.

the processing means are designed to determine the slope of the current changes at the start of each voltage pulse.

the processing means are designed to determine the time that passes between the start of the pulse and the instant at which the value of the current has stabilised.

the acquisition means and at least one part of the means of power are provided in a mobile unit equipped with a plurality of connectors for the electrodes, the processing means are incorporated into the mobile unit or provided in a computer that is separate from the said mobile unit, and a communication channel is provided between the mobile unit and the computer.

the communication channel is wireless.

According to another aspect, the invention proposes a dynamic diagnosis system, characterised in that it includes, in combination:

server means;

a plurality of analysis systems as defined above, connected to the server means by communication channels;

means to collect data relating to the current changes measured by the analysis systems on patients for which clinical diagnoses are prepared beforehand, in association with data that are representative of the said diagnoses prepared beforehand;

means for the control of algorithms provided in the server means, and executed periodically using the new collected data in order to validate pre-selected diagnosis algorithms and to identify new diagnoses.

Advantageously, this system also includes means for the transfer, to the analysis systems, of the newly validated or identified algorithms, in association with information relating to the pathologies or pathological predispositions that they are capable of detecting.

According to another aspect, a method of electrophysiological examination according to the invention is proposed for the detection of pathologies, characterised in that it includes the following steps:

successive application to a plurality of pairs of surface electrodes (E1-E4) positioned at distant parts of the human body, of essentially continuous voltage pulses of between about 1 and 5 volts and with a length of between about 0.1 and 5 seconds, recording of changes in the current flowing in the different electrode pairs to which these voltage pulses are applied, validation of the changes in the acquired current readings by comparison between at least two current changes provoked in conditions that are assumed to be identical, and comparing of data relating to the current changes as recorded for several electrode pairs and validated with reference data, thereby to give an indication of a pathological nature.

Certain preferred but non-limiting aspects of this method are indicated below:

the recording step is executed by sampling the current signal at a rate of between about 20 and 10,000 times per second.

the step for application of voltage pulses includes the application, to a given electrode pair, of voltage pulses of opposite sign.

the method includes a step for adjustment of the continuous voltage levels of the pulses.

the method includes a step for adjusting the length of the pulses.

the validation step includes comparison of the current changes obtained for several series of voltage pulses applied several times to the electrodes, and validation of these changes if a difference below a given threshold is observed.

the method also includes a step that consists of generating graphical representations of the current changes for the different electrode pairs, and corresponding graphical representations of the reference data.

the method also includes a step that consists of determining the slope of the current changes at the start of each voltage pulse.

the method also includes a step that consists of determining the time that passes between the start of the pulse and the instant at which the value of the current stabilises.

In one particular application, a method according to the invention is proposed for the detection of coronary problems, in particular by electrophysiological examination, characterised in that it includes the following steps:

(a) before the execution of any given exercise by a subject, successive application, to a plurality of pairs of surface electrodes (E1-E4), positioned at least in the region of the hands and in the region of the forehead of the subject, of essentially continuous voltage pulses of between about 1 and 5 volts and with a length of between about 0.1 and 5 seconds:

(b) recording of changes in the current flowing in the different electrode pairs as these voltage pulses are applied, (c) repetition of steps (a) and (b) after the subject has performed the said exercise, (d) comparison of the data relating to the current changes as recorded for the electrode pairs before and after the exercise, and (e) in accordance with the results of step (d), provision of a predictive indication of affection or non-affection.

Advantageously, step (e) is implemented by comparison of the increase in the electrochemical conductance, revealed by the current changes between the moment preceding the exercise and the moment following the exercise, at least for the hand electrode pair and the forehead electrode pair, with respective thresholds.

Finally, the invention includes application of the method, as specified above, to the detection of diabetic problems.

Figure 2:
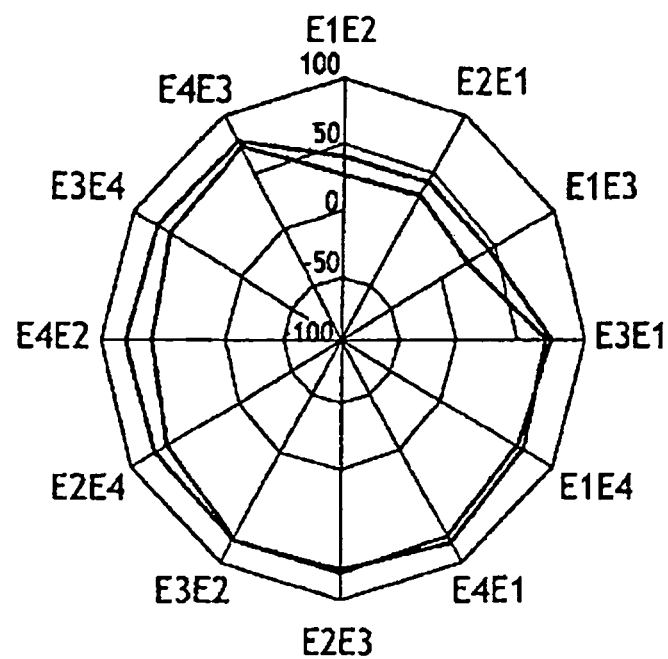
Figure 3:
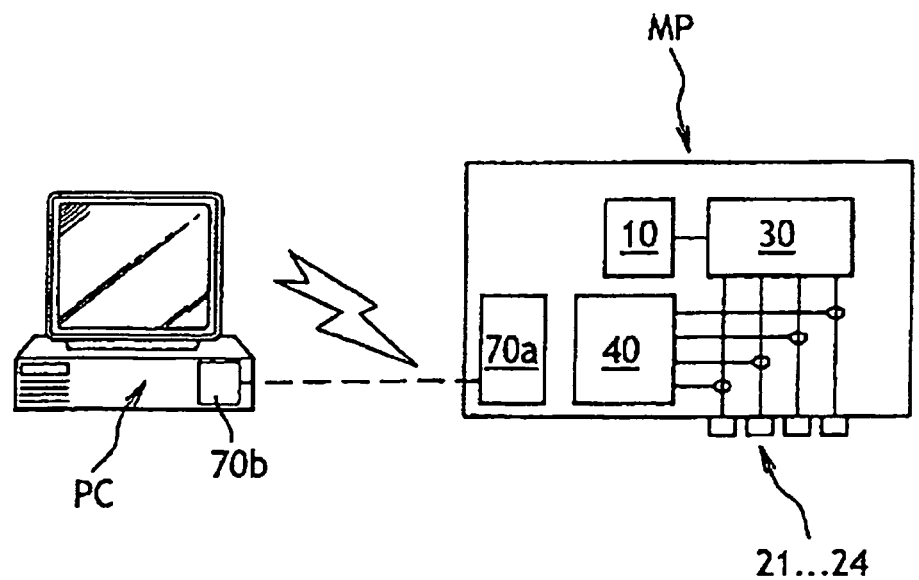
Figure 4:
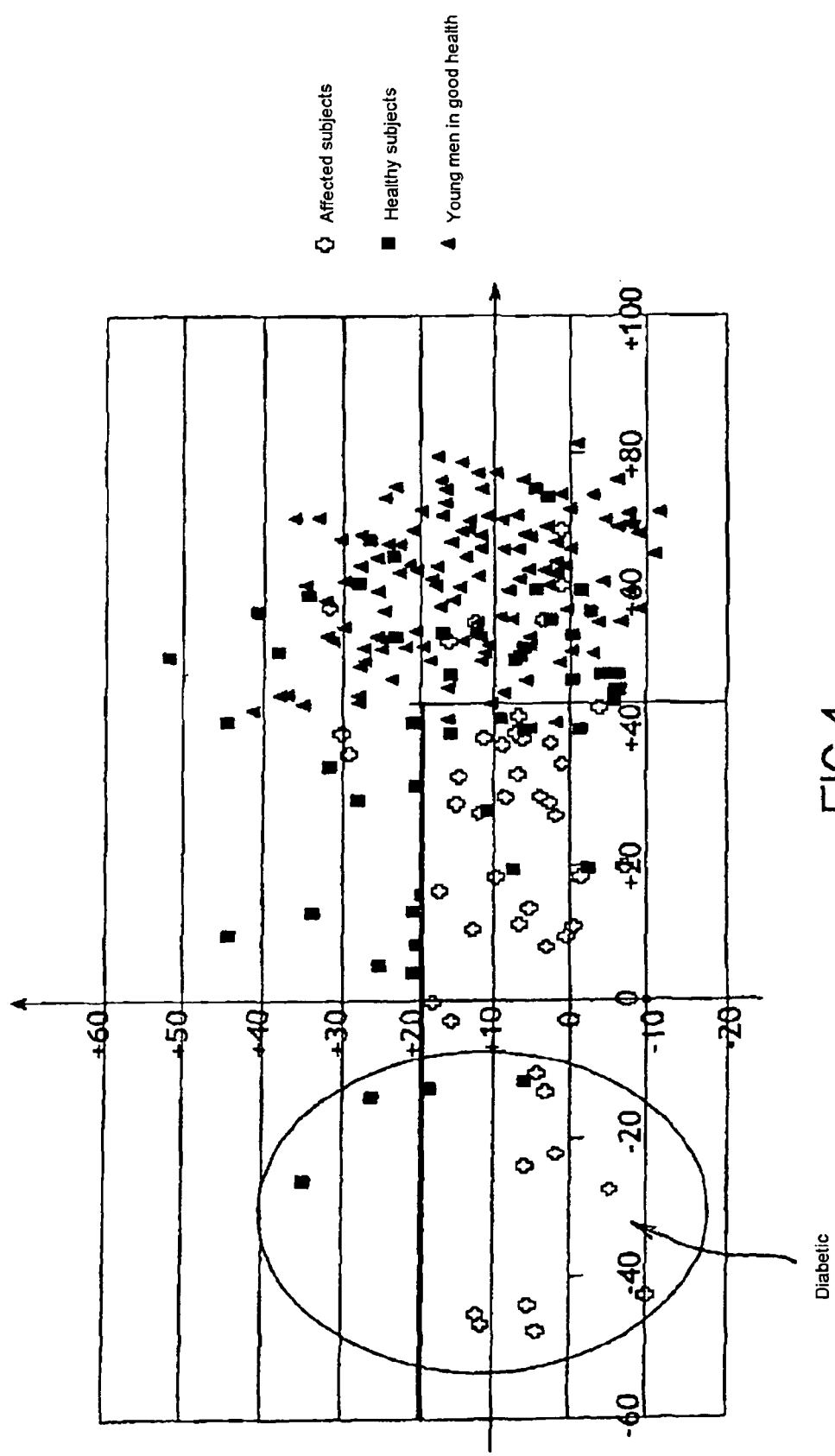

Other aspects, aims and advantages of this present invention will appear more clearly on reading the detailed description that follows of preferred embodiments of the latter, given by way of non-limiting examples, and with reference to the appended drawings, in which:

FIG. 1 is a block diagram illustrating the different functional elements of a system according to this present invention, FIG. 2 illustrates a graphical example of the radar type obtained with a system according to this present invention, FIG. 3 is a modified block diagram, illustrating the arrangement of a system according to the invention in two parts, and FIG. 4 is a graph illustrating the current readings obtained with a system according to this present invention, in the context of diagnosing coronary affections by means of the exercise test.

A description will now be given of a diagnosis system using electrophysiological measurements according to the invention. This system is based on an active operation principle, in direct current mode as opposed to the impedance measuring systems of the prior art, whose drawbacks were described above.

It will be seen firstly that the Applicant has conducted in-depth research into the electrical behaviour of the cells of the human body and their environment. It was observed that an alternating electrical current, particularly at low frequency, flowed only in the interstitial water (interstitium) separating the cells, and practically not at all through the water of the cells themselves. In fact the membranes of the cells have a sufficient capacitive effect to attenuate, practically completely, the alternating current at the low frequencies.

Other research on the behaviour of the membranes of the cells have been used to demonstrate that they behave very differently according to the nature of the interstitium, in particular its pH and its electrical potential.

To use these properties, it is possible to temporarily subject these environments to different conditions of potential and pH, and to measure their responsiveness.

One of these possibilities will now be explained.

It is firstly recalled that chloride ions have the property, in the presence of water and a sufficient difference of potential and in presence of a pH of less than 7.5, of converting to HCLO and $H_3O^+$, delivering two electrons.

On the other hand, for pH greater than 7.5, the formation of $CLO^-$ ions is observed.

These transformations can take place only above a critical voltage that depends on the respective concentrations of $Cl^-$ and HCLO and on the value of the pH. This voltage is typically about 0.8V in the usual physiological conditions.

It appears that this critical voltage rises when the pH reduces and when the concentration of HCLO increases, so that in the course of a measurement on living tissue, a halting of this transformation is attained more or less rapidly according to the initial voltage applied, the initial value of the pH, and the behaviour of the concentrations of $H^+$ and HCLO ions.

By means of the Cottrel chronoamperometry equation, this type of measurement is therefore used not only to gain access to the local concentrations of chloride ions but also to test the responsiveness of the tissue in vivo to a local increase in acidity.

In fact without the presence of natural buffers such as bicarbonates (or other), this transformation of chloride ions would result in very sharp drops in pH, which in turn would themselves lead to a very rapid halting of the reaction and therefore of the resulting current.

This reaction therefore also provides an indirect means of locally testing the state of the acid/alkali balance of the living being, namely the ability of the natural buffers to fulfil their role.

Given that the chloride ion is the anion most present in the extracellular compartments of living organisms, it is therefore possible to estimate, in real time and in vivo, and at various parts of the body such as the hands, the soles of the feet, the forehead, etc., the ionic nature of the interstitium.

These measurements of chloride concentrations and responsiveness of the acid/alkali balance can be used to trace homeostatic, hormonal, vascular, metabolic and other malfunctions. These malfunctions can themselves correspond to various pathologies or pathological predispositions, and in particular:

vascular predispositions (hypertension and extensive atheroma, coronary affections, etc.);
hormonal predispositions (hypo- and hyper-thyroid conditions, etc.)
metabolic predispositions (diabetes, etc.).

The invention, as it will now be described in detail, aims to exploit the electrochemical techniques of chrono-amperometry or voltammetry to measure the currents generated in the aforementioned electrochemical reactions and thus to estimate, in a realistic manner, the conditions that exist in the interstitium, which themselves are then used to describe the physiological state of living beings.

It will now be noted that corrections may be necessary in accordance with the voltages actually applied and measured on the electrodes, in order to take account of the reverse currents that are liable to be generated if a voltage in excess of 0.8 volts appears on the distal electrode.

FIG. 1 schematically represents a system of diagnosis by electrophysiological measurements that can be used to exploit the aforementioned principles, which includes, in an appropriate cabinet (not shown), a stabilised low voltage supply circuit 10 (typically a voltage that can be adjusted from about 1 to 5 volts) and that is suitable to be connected, as will be seen in what follows, to connectors 21 to 24 for a plurality of corporal electrodes (typically 4 to 8 in number).

In an example of application, four electrodes (E1 to E4) are placed on the four members, that is on the hands and feet respectively. It will be seen that there are 6 possible pairs of usable electrodes, namely E1-E2, E1-E3, E1-E4, E2-E3, E2-E4 and E3-E4.

In order that the current measurements effected using the electrodes should suitably reflect the electrochemical behaviour of the interstitium, it is important that these electrodes each have a significant area, and preferably between about 1 and 15 cm$^2$.

Using an electronic switching circuit 30, one applies sequentially to these electrode pairs, continuous voltage pulses with a value that is chosen to be between 1 and 5 volts, where these pulses can be positive or negative by simple reversal of polarity.

We thus obtain 12 possibilities for measurement of the current changes that traverse the body between two electrodes when the continuous voltage pulse waveform is applied. The switching circuit is controlled by a clock 31, in a manner that can easily be understood by the those skilled in the art.

The system also includes an acquisition circuit (sampling and analogue/digital conversion) 40 which, on application of a continuous voltage pulse waveform, is designed to store the values taken by the current at predetermined short time intervals.

For example, the system can generate a continuous voltage pulse waveform for a time of between 0.1 and 5 seconds (typically 3 seconds), and during the existence of this pulse, samples are taken of the current every millisecond. More generally, a sampling frequency of between 20 and 10,000 samples per second is employed.

The system then switches to the next electrode pair to repeat the process, and so on.

The system also includes a processing device or arrangement 50 with a view to analysis of the values acquired during the process described above, where this device typically includes a processor in association with a memory. It is connected to indicating means (display screen, printer, or any other indicating device) for the operator.

Preferably, this device or arrangement is designed firstly to perform a set of tests for validation of the measurements on the values of current collected by the sampling circuit 40.

A first test aims to determine if the measurements effected are normal, and to reject any measurements containing errors or anomalies such that they must be non-meaningful.

This first test is performed on completion of 36 sets of measurements, namely the 12 measurements described above, effected here in three passages. Here we describe, as a curve, the set of measurements of the current obtained for each continuous voltage pulse waveform.

For each of the 36 curves, the device stores the values of the samples of the first two samples read and digitised, and also calculates an average of the first twelve samples.

The device then determines whether, for each curve, the averages calculated for each of the second and third passages are identical to each other to within x %, where x is preferably between 1 and 10%.

In the case where, for at least one of the curves, the difference between the averages is above this limit, then the set of 36 curves is rejected.

If the set of curves passes the first test above, the processing device (50) does a second validity test that consists of checking whether the last X values (where X is of the order of a few units to a few tens of units) of the second and third sets of measurements are close to each other with a given margin of error, also preferably of the order of 1 to 10%.

In the affirmative, the measurements are considered to be valid.

Naturally any other combinations of the current values taken can be used to determine the validity of the measurements.

In the negative, then all the equipment is checked (positioning and stability of the electrodes in particular) and the campaign of measurements is repeated.

From the validated measurements, the device then performs a more-or-less complex transformation that is intended to guarantee the intrinsic reproducibility of the data collected. In this present example, this transformation consists of taking the mean, over the three seconds that each pulse lasts here, of each of the 12 curves of the last (here the third) passage, and generates output information to be displayed on a diagram of the so-called radar type, where this diagram also includes, in a manner stored beforehand in the system, measurement templates corresponding to healthy patients and sick patients. An example of such a radar diagram is illustrated in FIG. 2 of the drawings. Naturally, many other transformations can be envisaged, in particular according to the characteristics of the current and the pathologies sought.

Such a diagram of the radar type is well known in terms of its ergonomic usefulness. It consists of distributing the results of the measurements obtained with the different electrode pairs in a polar coordinate system, where a given angular position is dedicated to the representation of a level of signal obtained (as a result of appropriate processing) for a given electrode pair as identified in the figure.

This has the advantage of giving a good visual indication of the similarities and differences between sets of measurements coming, for example, from different patients or from the same patient at different times, and to facilitate the comparison with templates of healthy patients and sick patients.

Other than the display intended for the operator, the processing device is also designed to effect a quantitative comparison between the measurements and the templates, using algorithms that are available to those skilled in the art.

In particular, if the template of a healthy person is exceeded at more than three points, or by more than X % (30% for example) at any point, the operator applies, to the processing device, a command for comparison with a template associated with a given pathology, and these comparisons are repeated until a template is found that conforms to the potential pathology.

Naturally, many other forms of embodiment and variants are possible. In particular, it is possible to vary the number of electrodes, and to make use of eight electrodes for example (four for the ends of the members, two for the forehead and two for the chest).

In particular in accordance with the possibilities (computing power and memory) of the processing device, it is possible to adjust the sampling period of the current measurement, with the latter being capable of descending to 0.1 ms for example (a sampling frequency of 10 kHz)

It is also possible to provide a variable sampling frequency that is higher at the start of the current measurements for a given pulse and lower at the end of the pulse.

The processing device can also be designed to provide a signal that is representative of the slope (derivative) of the current signal just after the start of the voltage pulse, and to calculate the time passed between the start of the voltage pulse and the instant at which, while the pulse lasts, the current stabilises (to within x %, where x is chosen in particular in accordance with the sampling precision).

Such values, which are determined for a given set of electrode pairs and polarity of the pulses, can then be compared to limit values, here again with the use of radar diagrams if appropriate.

More generally, different types of algorithms can be executed in order to process the N lots of curves (according to the number of electrodes and successive tests) to validate finer sensitivity and specificity curves by comparison with Receiver Operating Characteristic (ROC) curves obtained with patients on which clinical tests have been validated.

According to another preferred characteristic, the processing circuit is designed to generate results obtained from a probability, according to algorithms which are also known to those skilled in the art. If the probability is not satisfactory, it is possible to re-run a measurement campaign with different voltage values (increasing for example) for each passage on all of the electrode pairs.

In this regard, the switching circuit 30, and the power-supply circuit 10 where appropriate in order to vary the voltage level, are advantageously programmable so as to be able to execute different measurement scenarios, with pulses of variable length (duration) and height (voltage level) if appropriate.

FIG. 3 illustrates one possible embodiment of a system according to the invention. This system is constructed around a conventional personal PC-type computer designed to communicate with a portable MP module that includes:
  the power source 10, if power is not supplied by the PC;
  the set of connectors 21 to 24 for the body electrodes;
  the switching circuit 30 used to apply, to the aforementioned connectors, voltage pulses according to one or more determined scenarios as explained above;
  the acquisition module 40 capable of sampling and digitising, at a given frequency or several given frequencies, as explained above, the current flowing from one electrode to another while this electrode pair is subjected to the voltage pulse,
  a buffer memory module 60 if necessary, to store the current measurements thus acquired;
  an interface or communication module 70a to communicate with the PC, either over a wire link (serial, USB, etc.), or via a wireless link (Bluetooth®, Wifi®, infrared, etc.).
  a set of electrodes E1 to E4 with their cables.

In such an architecture, the processing device 50 for the current measurements received from the portable unit is constituted by the PC, which includes an interface or communication module 70b providing the link with the portable module.

Advantageously, the PC has the means to communicate with one or more public or private servers, from which templates of healthy or sick patients can be transferred for purposes of comparison as described in the foregoing, and/or to which the information generated by the processing device 40 can be sent.

On this subject, a description will now be given of a real-time or semi-real-time system for the processing of clinical data obtained from data supplied by a diagnosis system such as that described in the foregoing.

More precisely, this aspect of the invention consists of exploiting the simplicity and specificity of the chronoamperometry measurements supplied by a set of diagnosis systems so as to be able to propose the most up-to-date information in real time or semi-real-time.

In a preferred embodiment, the process includes the following essential steps:
  approval from a certain number of reference clinical centres, equipped with the diagnosis system and connected by an appropriate communication system to a central server or distributed servers (subscriber systems with the possibility of payment for each transaction);
  centralisation, at the level of the server or servers, preferably with a daily frequency at least, of the measurements effected on patients for which well established and standardised clinical diagnoses are held, where these measurements are accompanied by data which are preferably structured or encoded, representing the said established clinical diagnoses;
  use of the database thus constituted, preferably with the following sub-steps:
  data validation, and more particularly statistical validation and verification of the application of normal laws;
  analyse of the consistency of the data (by correlation methods in particular) and treatment of any excessive differences with specific surveys by staff who are skilled on these data;
  a search for algorithms that are relevant to the data, and more particularly from set of known algorithm tests and stored beforehand in the server or servers and based in particular on the following tools:

approach by the Bayes theorem (Bayesian networks);
approach by multiple neurone networks with at least two layers
approach by decision trees;
approach by genetic algorithms;
comparison of the results produced by these algorithms with the existing diagnostic knowledge;
where appropriate, comparison of the collected data with pre-existing data using other rules such as classification rules;
validation of existing algorithms, using each new data lots as an estimator of the predictive positive and negative values for each pathology or pathological predisposition selected as capable of being diagnosed;
validation of new algorithms identified and representative of a new diagnostic knowledge on all of the data previously existing in the database.

Preferably, all of the process described above, from loading of the data from the distant diagnosis systems up to the validations of existing and new algorithms, is automated, with only detected errors being subject to particular indication for examination by competent experts.

All of the foregoing processes for collection and analysis are effected on a daily basis at least for example, and so they supply an up-to-date service practically in real time, with the new diagnostic features identified by these processes.

According to one advantageous aspect, in the case where the local diagnosis systems possess the appropriate processing capacity, these new features (new algorithms and the information on their diagnostic role for the use of practicians) are advantageously downloaded from servers to the subscriber systems (with secure unitary payment at the moment of the transaction) when they have been identified, in accordance with conventional computer techniques for the updating of software or of their libraries, plug-ins or other associated modules.

In a non-limiting manner, the system of the invention can be used for the diagnosis of pathologies of the cardiac, endocrinal, or neurological or other type.

One particular application of this present invention is diagnosis by the exercise test on patients suffering from Coronary Artery Disease (CAD).

EXAMPLE

In a population of 95 men chosen at random, with ages between 21 and 83 years and an average age of 57 years, this present invention was used to detect angiocoronarographical affections of the arteries. The chronoamperometric measurements, effected using the system of this present invention, were taken before and after the exercise test, conducted according to the Bruce protocol. The population included subjects identified as suffering from affection, and other subjects identified as healthy. The affected population was also broken down into subjects suffering from diabetes and into subjects without diabetic affection.

In this case, the system of the invention included two surface electrodes applied to the hands and two other surface electrodes placed on the head at the left and right frontal lobes.

The currents appearing in response to the voltage pulses, indicating electrochemical reactions in accordance with Cottrell law, are stored. The currents between the two electrodes of the hands are read off, as are the currents between the two electrodes on the forehead.

The total time taken to collect the current measurements was less than 1 minute.

The graph shown in FIG. 4 of the drawings shows a set of test points whose coordinates are the relative electrochemical conductance obtained between the electrodes on the hands (abscissa) and between the electrodes on the forehead (ordinate) for the different subjects.

It will be seen here that the relative electrochemical conductance is the difference, positive or negative, of the absolute electrochemical conductance read off using this present invention, before the exercise and after the exercise, according to the Bruce protocol.

Among the subjects are the aforementioned population of 95 affected and healthy subjects, where the measurements corresponding to the healthy subjects are illustrated by squares and the measurements corresponding to the subjects with an affection are illustrated by circles.

FIG. 4 also shows the measurements obtained with a population of 150 young men in good health, normally with no coronary affection.

The graph in FIG. 4 shows that the system and the method of this present invention can be used to obtain a diagnosis specificity of about 82% and a diagnosis sensitivity of about 83%, leading to a positive prediction value of 81% and to a negative prediction value of 83% (5% risk intervals less than 10%). The corresponding thresholds have been identified at about +43% for the electrochemical conductance at the hands and about +19% for the electrochemical conductance at the forehead.

It can be seen here that the age, the body mass index (BMI), the current medicinal treatments, the offset of the ST segment, and other parameters associated with the exercise test, had no significant influence on the results.

It can also be seen from the readings in FIG. 4 that the group of 14 subjects identified beforehand as diabetic is also very localised, with a threshold of relative electrochemical conductance at the hands of less than −6%, thus allowing the diagnosis function to be enriched without any additional operation.

The population of 150 healthy young men shown in FIG. 4 confirms the validity of the identified criteria, with a negative prediction value greater than 90%.

Advantageously, a diagnosis system by analysis of the currents before and after exercise can be incorporated into exercise equipment in commercial centres, such as home exercise machines, running tracks, etc., allowing the subject to directly assess his or her predisposition to coronary problems, by simple application of electrodes to the wrists and forehead, at home or in the gymnasium, and with no need of a specialist.

From the foregoing information, those skilled in the art will be able to develop diagnosis systems for a wide variety of pathologies or pathological predispositions, essentially by examining the measurements produced by the system and the method of this present invention, on populations of healthy or sick subjects respectively.

The invention claimed is:

1. An electrophysiological examination system for detection of pathologies, comprising:
a plurality of surface electrodes designed to be positioned in direct skin-to-electrode contact with distant parts of a human body where each surface electrode of the plurality of surface electrodes has a significant area ranging from 1 square centimeter to 15 square centimeters,
a power supply operable to be selectively electrically coupled in succession to form sets of electrode pairs of the plurality of electrodes to apply continuous DC voltage pulses ranging from 1 to 5 volts with a duration ranging from 0.1 to 5 seconds to the sets of electrode pairs, wherein the applied DC voltage pulses are adapted to induce electrochemical changes in the human body including production of chloride ions which affects current flowing in the sets of electrode pairs when the electrophysiological examination system is in use, an acquisition and storage circuit to record current changes flowing in the several sets of electrode pairs as the continuous DC voltage pulses are applied, the acquisition and storage circuit having a sampling circuit configured to sample current signals at a rate ranging from 20 to 10,000 times per second, and a processor configured to compare at least two current changes to validate the changes in the recorded current readings by comparison between at least two current changes provoked in conditions that are assumed to be identical, the processor configured to compare data relating to the recorded and validated current changes with reference data, and thereby produce an output indicative of a pathological nature.

2. The system according to claim 1, wherein the power supply includes a switching circuit to apply, to a given electrode pair, voltage pulses of opposite sign.

3. The system according to claim 1, wherein the power supply is programmable to adjust voltage levels of the pulses.

4. The system according to claim 3, wherein the power supply is programmable to adjust the duration of the pulses.

5. The system according to claim 1, wherein the processing device is operably configured to compare current changes obtained for several series of voltage pulses applied several times to the electrodes, and to validate these changes if a difference below a given threshold is observed.

6. The system according to claim 1, further comprising an output device operably configured to generate graphical representations of the current changes in the several sets of electrode pairs, and corresponding graphical representations of the reference data.

7. The system according to claim 1, wherein the processing device is operably configured to determine a slope of current changes at a start of each voltage pulse.

8. The system according to claim 1, wherein the processing device is operably configured to determine a time that passes between a start of the pulse and an instant at which the value of a current stabilises.

9. The system according to claim 1, wherein the acquisition and storage circuit and at least part of the power supply are provided in a mobile unit that is equipped with a plurality of connectors for the electrodes, and wherein the processing device comprises a computer that is separate from the mobile unit, and wherein a communication channel is provided between the mobile unit and the computer.

10. The system according to claim 9, wherein the communication channel is wireless.

11. The system according to claim 1, further comprising:
a server;
a network of multiple ones of the electrophysiological examination system set forth in claim 1 where the multiple electrophysiological examination systems are separated from each other and have a mobile connection to the server by communication channels;
the server being programmed to collect data relating to the current changes measured by the acquisition and storage circuit on patients whose clinical diagnoses are established beforehand, in association with data representing the said diagnoses prepared beforehand; and
the server being programmed to control algorithms provided in the server, and to execute the algorithms periodically using newly collected data in order to validate pre-selected diagnosis algorithms and to identify new diagnoses.

12. The system according to claim 11, wherein the communication channels are two way, thereby enabling transfer of newly validated ones of the pre-selected diagnosis algorithms to the multiple electrophysiological examination systems, in association with pathologies or pathological predispositions that the multiple electrophysiological examination systems are capable of detecting.

13. An electrophysiological examination system for detection of pathologies in a patient comprising:
a plurality of surface electrodes each adapted to be positioned in direct contact with a skin surface of the patient when the electrophysiological examination system is in use, each surface electrode of the plurality of surface electrodes having a significant area of at least 1 square centimeter,
a DC power supply operably and selectively electrically coupled in succession to several sets of electrode pairs of the plurality of electrodes to apply pulses of continuous DC voltage ranging from 1 to 5 volts and having a duration ranging from 0.1 to 5 seconds to the electrode pairs, wherein the several sets of electrode pairs include a first pair of electrodes including a first electrode positioned at a distant body part of the patient from a second electrode of the first pair of electrodes,
an acquisition and storage circuit to record current changes flowing in the several sets of electrode pairs as the pulses of continuous DC voltage are applied, and
a processing device configured to compare changes in the recorded current readings between at least two current changes provoked in conditions that are assumed to be identical, and the processing device operably configured to compare data relating to the recorded and validated current changes with reference data, and thereby produce a signal indicative of a pathological nature.

14. The system according to claim 13, wherein the significant area of the plurality of surface electrodes covers palm surfaces and sole surfaces of the patient when the plurality of electrodes are positioned in direct contact with hands and feet of the patient.

15. The system according to claim 14, wherein the first electrode is adapted to be positioned in direct contact with one of the hands of the patient and the second electrode is adapted to be positioned in direct contact with one of the feet of the patient.

16. The system according to claim 14, wherein the several sets of electrode pairs include a second pair of electrodes and wherein the first pair of electrodes are adapted to be positioned in direct contact with the hands of the patient and the second pair of electrodes are adapted to be positioned in direct contact with the feet of the patient.

17. The system according to claim 13, wherein the plurality of surface electrodes are adapted to be positioned in direct contact with at least two body parts chosen from a group of: left and right hands of the patient, left and right feet of the patient, and a forehead of the patient.

18. The system according to claim 13, wherein the pulses of continuous DC voltage, that the DC power supply is configured to apply to the plurality of surface electrodes, exhibit a square waveform.

19. The system according to claim 13, wherein the acquisition and storage circuit is configured to record current changes flowing in the several sets of electrode pairs over a total time period having a duration that is less than 1 minute.

20. The system according to claim 13, wherein the plurality of surface electrodes are reusable.

* * * * *